(12) United States Patent
Quincy, III et al.

(10) Patent No.: US 9,078,742 B2
(45) Date of Patent: Jul. 14, 2015

(54) SELF-ACTIVATED COOLING DEVICE

(75) Inventors: Roger B. Quincy, III, Cumming, GA (US); Robert D. Wright, Peachtree City, GA (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 2680 days.

(21) Appl. No.: 11/639,867

(22) Filed: Dec. 15, 2006

(65) Prior Publication Data

US 2008/0147153 A1 Jun. 19, 2008

(51) Int. Cl.
F25D 5/00 (2006.01)
F25D 3/08 (2006.01)
A61F 7/10 (2006.01)
F25D 5/02 (2006.01)
A61F 7/03 (2006.01)
C09K 5/18 (2006.01)
F25D 31/00 (2006.01)
A61F 7/00 (2006.01)
A61F 7/02 (2006.01)

(52) U.S. Cl.
CPC . *A61F 7/106* (2013.01); *A61F 7/03* (2013.01); *C09K 5/18* (2013.01); *F25D 5/02* (2013.01); *A61F 2007/0001* (2013.01); *A61F 2007/0246* (2013.01); *A61F 2007/0276* (2013.01); *F25D 31/007* (2013.01)

(58) Field of Classification Search
CPC ... A61F 7/03; A61F 7/106; A61F 2007/0246; A61F 2007/0276; A61F 2007/0001; F25D 5/00; F25D 31/0072
USPC ....................................................... 62/4, 530
See application file for complete search history.

(56) References Cited

U.S. PATENT DOCUMENTS

| 4,462,224 | A | 7/1984 | Dunshee et al. |
| 5,681,298 | A | 10/1997 | Brunner et al. |
| 6,099,555 | A | 8/2000 | Sabin |
| 6,164,487 | A | 12/2000 | Hicks |
| 6,290,091 | B1 | 9/2001 | Bell |

(Continued)

FOREIGN PATENT DOCUMENTS

| WO | WO 01/03619 | 1/2001 |
| WO | WO 2004/105709 A1 | 12/2004 |

OTHER PUBLICATIONS

Search Report, Feb. 21, 2008.

(Continued)

*Primary Examiner* — Frantz Jules
*Assistant Examiner* — Webeshet Mengesha
(74) *Attorney, Agent, or Firm* — Dority & Manning, P.A.

(57) ABSTRACT

A cooling device for placement against a body part or object includes a shell member having an outer face and an inner face disposed against a surface to be cooled. A first cooling substrate is disposed within the shell member and is an absorbent web having a generally uniform application of a first cooling composition applied thereto, the cooling composition activated by contact with an aqueous liquid. An aqueous liquid source is disposed within the shell member and is separated from the first cooling substrate by a barrier member. The device is activated by manual manipulation to breach the barrier member causing liquid from the liquid source to move within the interior space of the shell member to contact and activate the cooling composition whereby a cooling reaction is generated.

12 Claims, 9 Drawing Sheets

(56) References Cited

U.S. PATENT DOCUMENTS

| | | |
|---|---|---|
| 6,484,514 B1 * | 11/2002 | Joseph et al. .................... 62/4 |
| 6,642,427 B2 | 11/2003 | Roe et al. |
| 6,701,720 B1 * | 3/2004 | Stone et al. .................... 62/4 |
| 2003/0075549 A1 | 4/2003 | O'Brien et al. |
| 2004/0116990 A1 | 6/2004 | Agarwal et al. |
| 2005/0136765 A1 | 6/2005 | Shannon |
| 2006/0154006 A1 | 7/2006 | Usui et al. |

OTHER PUBLICATIONS

Co-Pending U.S. Appl. No. 11/639,967, filed Dec. 15, 2006.

* cited by examiner

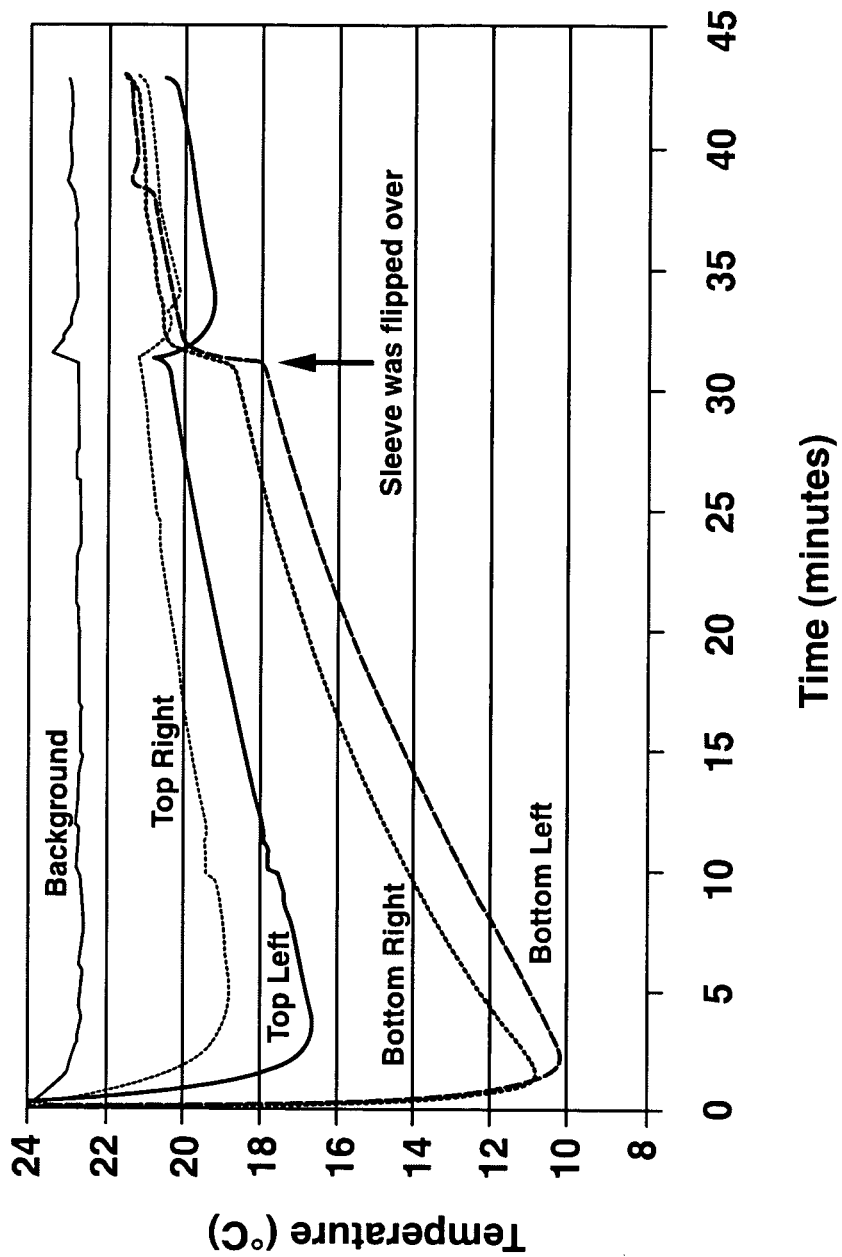

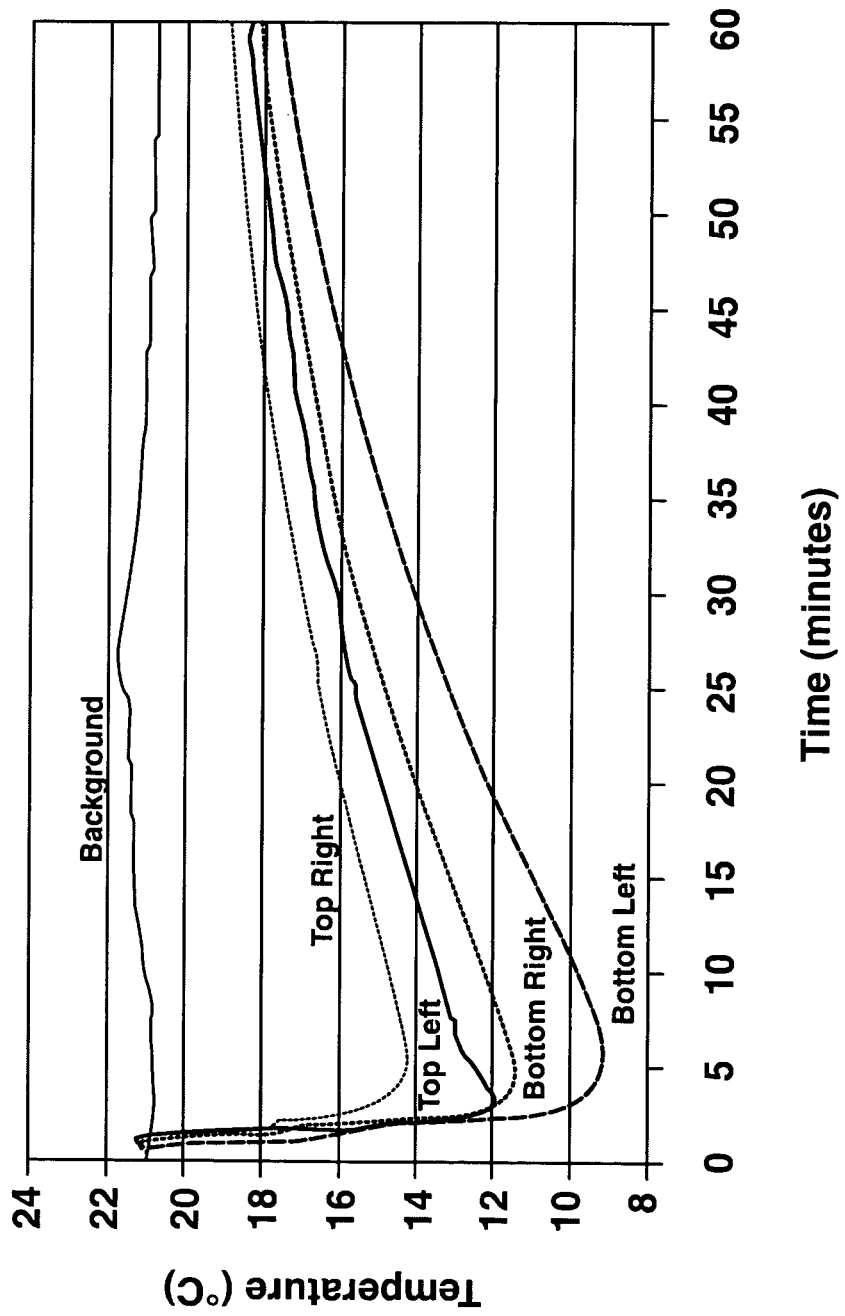

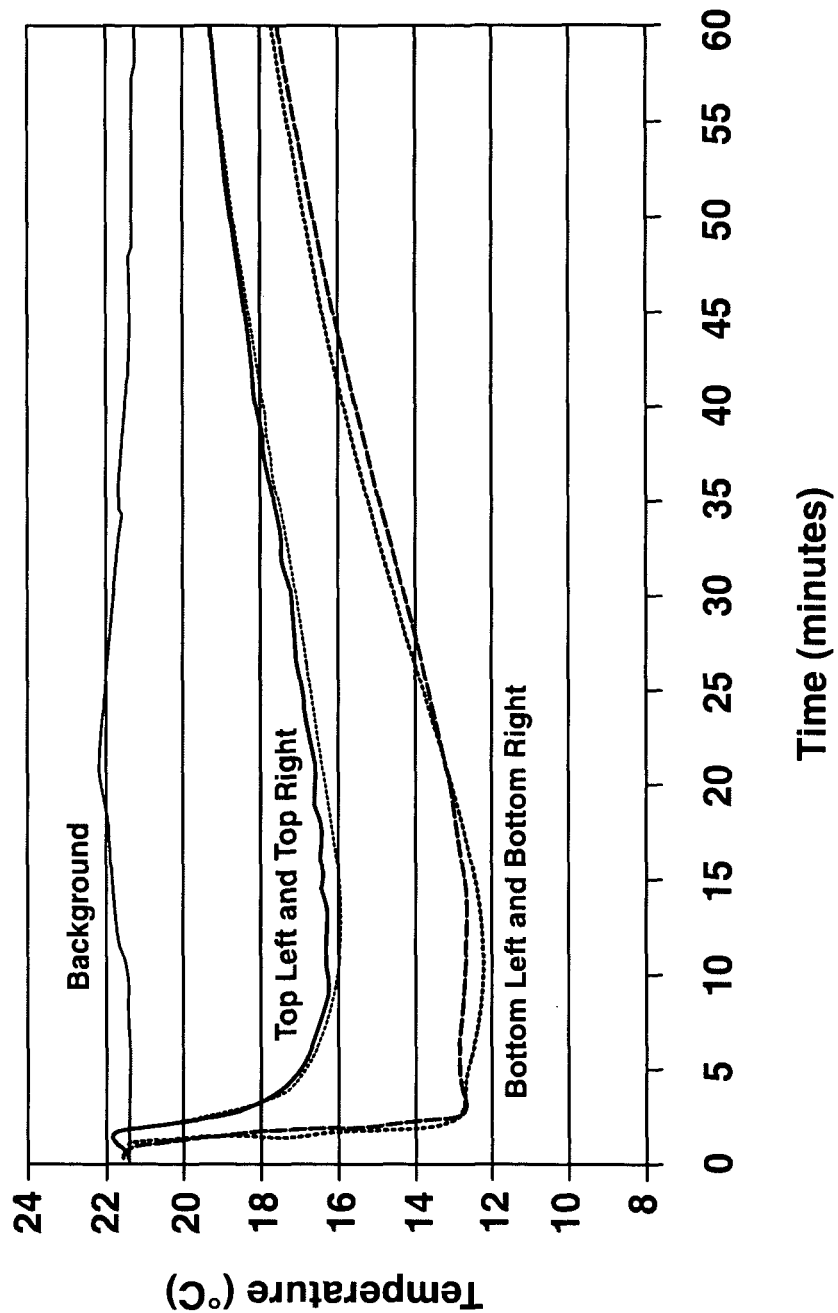

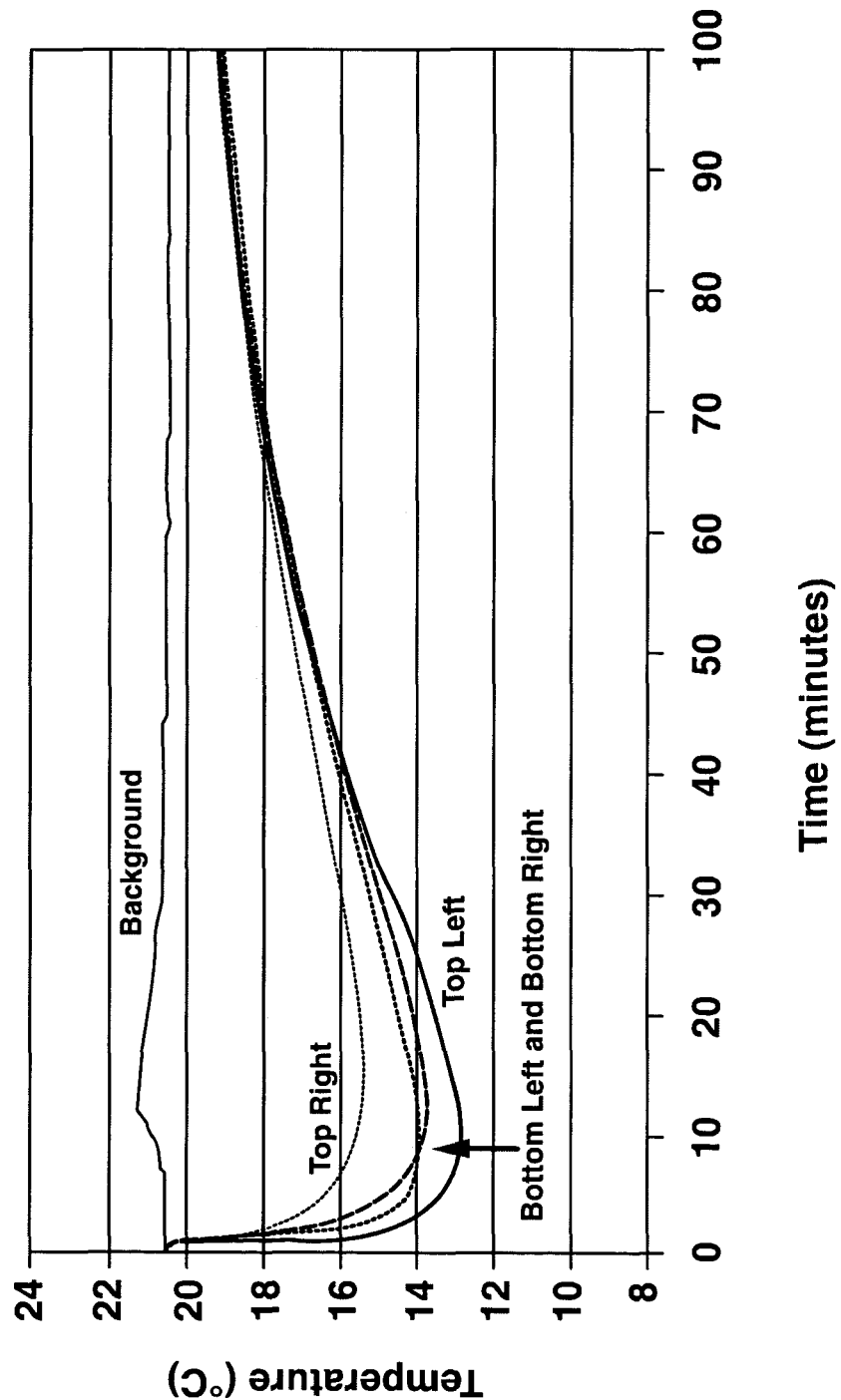

SELF-ACTIVATED COOLING DEVICE

BACKGROUND OF THE INVENTION

Thermal cooling wraps or packs are well known in the art for providing any manner of therapeutic or soothing cooling to a person. For example, such devices are typically used to treat sports injuries, or used in various medical procedures to cool a patient. Conventional self-contained cooling packs are available that contain particles of a cooling agent, such as urea or ammonium nitrate, separated from a compartment or pouch that contains an aqueous liquid. Typically, the cooling function is achieved by breaking or rupturing a barrier or seal between the liquid and cooling agent particles. As the particles dissolve in the aqueous liquid, heat is absorbed and a cooling effect is generated. Such devices are widely used in the medical industry, and in the transport and storage of food products.

U.S. Pat. No. 6,099,555 describes a gelling cold pack that includes a gelling agent, such as starch, adhered as a liquid permeable non-continuous coating to a composite particulate "cold-generating" material that interacts with a liquid to produce cold. The cold-generating material may be one of a number of ammonium salts, tin, cobalt or nickel salts, alkali metal salts, or an organic compound such as urea. The gelling material is applied to the cold-generating particles by spraying, dipping, brushing or with the use of an adhesive material. The coated particles are housed in liquid-impermeable, heat-conducting zones of a disposable container, with at least one other zone containing a liquid. The cold pack is activated by rupturing a frangible membrane between the zones. These and similar cold packs are designed to be placed into containers to cool food or drinks. Such cold packs also have a number of medical applications, including therapeutic devices for relief from overheating, wound care, treatment of strained muscles, joints or ligaments, or to treat or prevent heat exhaustion.

U.S. patent application 2005/0136765 describes various fibrous sheet materials, such as tissue and paper towels, provided with chemical agents, such as certain salts, that create a temperature change in the sheet when exposed to water. When water is absorbed by the sheet, the salt dissolves and produces a cooling or warming temperature change depending on the particular salt. The sheets may be used for wiping the hands, face, and body since the temperature change can be initiated by absorption of body fluids, such as sweat or surface moisture on the skin.

WO 2004/105709 describes various types of self-warming skin care compositions that include a heat generating powder coated with a combination of oils and/or waxes to partially delay the onset of the exothermic reaction and extend the duration of the warming effect. The heat generated in the exothermic reaction of the powder with water warms the skin, enhances cleansing, and may provide improved blood circulation. The heat generating powder may be an inorganic salt, such as calcium chloride, magnesium chloride, magnesium sulphate, and the like.

Unfortunately, various problems arise when attempting to apply an endothermic or exothermic composition to a substrate. Specifically, if the composition were exposed to moisture during application or storage, the reaction could occur prematurely. Certain salts are susceptible to absorbing moisture from the air and may slowly warm or cool over time until an equilibrium moisture state is reached. This ultimately would lower the quality of the composition and degrade the desired effect of any device incorporating the composition. Also, it is difficult to apply the compositions to substrates in an effective and uniform concentration that yields the desired result, particularly a sustained and controlled reaction as compared to a rapid, short duration temperature change.

As such, the art is continuously seeking improved thermal cooling devices that are simple, effective, relatively inexpensive to make, and produce a controlled and sustained cooling effect.

SUMMARY OF THE INVENTION

Objects and advantages of the invention will be set forth in part in the following description, or may be obvious from the description, or may be learned through practice of the invention.

In accordance with one embodiment of the present invention, a cooling substrate combination is provided. The combination is not limited by its intended use, and may find utility in the medical arts as a component of a patient cooling or therapeutic device, or in the recreational arts for use in a beverage or food cooler, and so forth. In particular embodiments, the substrate combination may be used as a component of a disposable single-use wrap or sleeve configured to be removably applied to any part of a person's body or other object to supply a cooling effect thereto.

In particular embodiments, the substrate combination includes a first absorbent web of a porous material having a first cooling composition applied thereto as a substantially film-like continuous network distributed throughout the porous material. The cooling composition includes a cooling agent that is activated by contact with an aqueous liquid, such as water, and a hydrophobic agent that is present in the composition in an effective amount to inhibit wetting of the substrate. By reducing the wettability of the substrate, the cooling reaction is controlled and prolonged when the substrate is contacted with the aqueous liquid.

The cooling composition may be applied to the absorbent web as an aqueous solution. In this manner, the solution impregnates and permeates throughout the porous material. The web is subsequently dried so that the solution dries into a substantially continuous film-like network throughout the porous material.

The cooling agent may include any one or combination of agents, including inorganic salts, organic material, and so forth. In particular embodiments, the cooling agent is ammonium nitrate or urea.

The hydrophobic agent may be any one or combination of polymer emulsions that are typically used as barrier coatings. A particular agent may be, for example, a wax emulsion or a vinyl acetate-ethylene copolymer.

It may also be useful to include a viscosity modifying agent in the cooling composition to aid in applying the composition in solution form to the porous material.

The concentration of cooling agent and hydrophobic agent in the cooling composition may vary depending on the desired cooling profile to be produced by the substrate, and may be readily empirically determined by those skilled in the art. For example, for a particular cooling profile, the cooling agent may be at least about 50% by weight of the cooling composition, and the hydrophobic agent may be between about 0.5% to about 10.0% by weight of the cooling composition. In an alternative embodiment, the cooling agent may be at least about 60% by weight of the cooling composition, and the hydrophobic agent may be at least about 5.0% by weight of the cooling composition.

The cooling substrate combination may be modified with any combination of absorbent webs and different cooling compositions to achieve varied cooling profiles. For example, the substrate combination may include a first absorbent web incorporating a first cooling composition with the hydrophobic agent to produce a less rapid but prolonged cooling profile. A second absorbent web may include the same or different cooling composition with less (or none) of the hydrophobic agent to produce a more rapid but shorter duration cooling profile. The combination of the two webs provides the substrate combination with a relatively rapid yet sustained cooling profile. It should thus be appreciated that the substrate combination may utilize any combination of individual absorbent webs and cooling compositions to produce a desired cooling effect.

It is also within the scope of the invention to include multiple cooling compositions on the same absorbent web to achieve a desired cooling profile. For example, a first cooling composition may be applied in a certain pattern over a particular section of the absorbent web. A second cooling composition may then be applied to a different section of the absorbent web. The combined effect of the two cooling compositions produces a unique cooling profile when an aqueous liquid is introduced to the web.

The present invention also includes any manner of cooling device that incorporates the various cooling substrate combinations discussed herein. For example, such a device may include a shell member having dimensions suited for the intended use of the device, such as a cooling therapeutic device applied to any part of a person's body. The shell may include an outer face and an inner face that is disposed against the surface to be cooled in use of the device. Any combination of the cooling substrates discussed herein may be disposed within an interior space in the shell member.

A source of aqueous liquid may be disposed within the interior space of the shell and is separated from the cooling substrate combination by a barrier member, such as a breakable wall, frangible seal, bladder or other breakable liquid container inserted into the shell member, or other suitable liquid source that is maintained separate from the cooling substrate combination. The device may be activated by simple manual manipulation of the shell member to break, rupture, or otherwise breach the barrier member to release the liquid from the liquid source. As the liquid moves through the interior space and contacts the cooling substrate combination, an endothermic cooling reaction is generated. The manual manipulation may include, for example, any combination of twisting, pulling, compressing, squeezing, or bunching of the shell member.

In one embodiment, the shell member may define a generally rigid configuration, such as an open or closed-end cylinder, that maintains its dimensions when not in use. For example, the shell member may include a layer of foam insulation material, or other material of sufficient thickness and rigidity such that the device maintains its cylindrical configuration without an article or body part being inserted therein.

In an alternate embodiment, the shell member is defined by a flexible sleeve member that is readily conformable around an object or body part, and assumes a generally flat or folded configuration when not in use. In this embodiment, the shell member may be formed by any combination of flexible and conformable materials. The cooling substrate combination is also formed from a flexible material so as to conform with the flexible sleeve. The flexible sleeve may be a planar component with any suitable attaching mechanism at one or both of the ends thereof so that the sleeve can be wrapped around and attached to an article or body part. In still another embodiment, the flexible sleeve may be formed into a continuous loop that is opened by the user to insert an arm, leg, or object into the device.

The cooling substrate combination may include a separate absorbent web that is placed into the interior space of the shell member, and may take on any size, shape, number, and configuration within the interior space of the shell member. For example, the cooling substrate combination may have dimensions essentially matching the interior length and width dimensions of the shell member. The substrate combination may include multiple absorbent webs separated by a material layer that serves to conduct fluid between the substrates.

In an alternative embodiment, the cooling substrate combination may include an interior layer of the shell member. For example, the shell member may be a laminate material having an absorbent nonwoven material layer exposed within the interior of the shell. This nonwoven layer may have the cooling composition applied thereto.

The cooling device may provide any desired cooling profile depending on the number and combination of cooling substrate combinations disposed within the device, as discussed above.

The liquid source within the interior space of the shell may take on various configurations. For instance, the source may be defined by a liquid-filled compartment defined within the shell, the compartment having a barrier wall or seal that is breached or opened by simple manual manipulation of the device. This compartment may be defined by one or more of the interior surfaces of the shell member. For example, a frangible wall may be attached at the longitudinal ends of the shell member between the opposite interior surfaces of the shell member, with this wall rupturing or breaking upon pressure being applied to the device. In another embodiment, the compartment may be defined entirely by the interior surfaces of the shell member, with a frangible seal between the surfaces separating the liquid compartment from the cooling substrate combination. In other embodiments, the liquid source includes any combination of separate liquid filled "bladders" or breakable containers placed within the interior of the shell. These bladders may include, for example, vials, pliable pouches, or any other suitable liquid container that is readily opened or breeched by external manual manipulation of the device.

Desirably, the amount of liquid released into the interior space of the shell member is calculated such that essentially all of the liquid is absorbed by the absorbent web components of the cooling substrate combination. In this manner, excess liquid is not held within said interior space after activation of said device.

Other features and aspects of the present invention are described in more detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which:

FIGS. 9A through 9D are time v. temperature charts for Examples 1, 4, 8, and 11, respectively.

DETAILED DESCRIPTION OF REPRESENTATIVE EMBODIMENTS

Figure 1A:
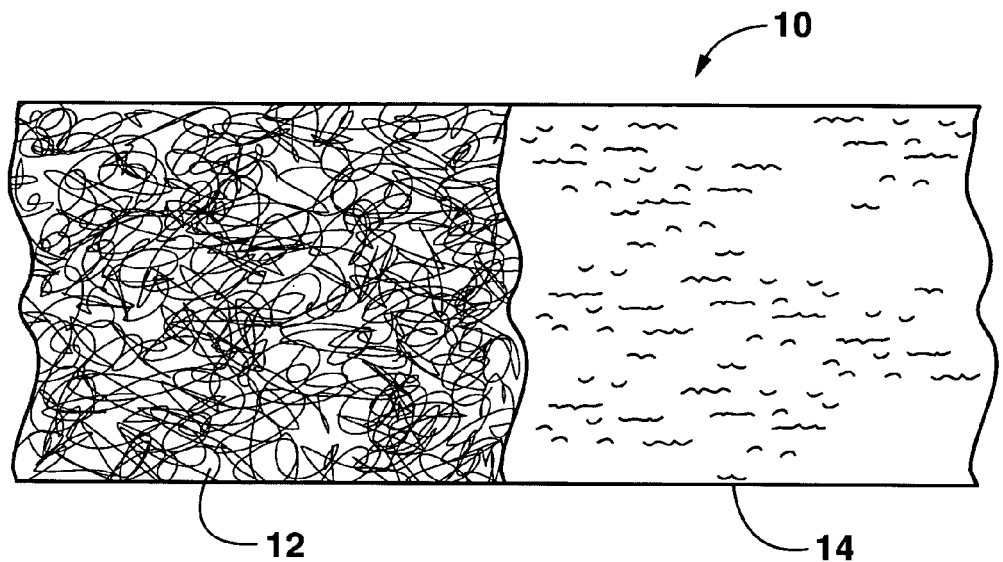
FIG. 1A is a perspective and partial cut-away view of an embodiment of a cooling substrate in accordance with the invention.

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

Generally speaking, the present invention is directed to a cooling substrate combination, and any manner of cooling device that incorporates the substrate combination, such as a sleeve or wrap to be applied against any desired body part or object. The cooling substrate combination includes an absorbent web having a cooling composition applied thereto that generates a cooling effect when exposed to an aqueous liquid, such as water. Through selective control of the cooling composition and supply of aqueous reactant, a desired cooling profile may be achieved in which a decreased temperature is reached quickly and maintained over an extended period of time.

The cooling composition may include any one or combination of known cooling agents that react with an aqueous liquid in a physical reaction that produces cold by the negative heat of dissolution of the agent into the aqueous liquid. For example, the dissolution in water of inorganic salts such as ammonium nitrate, potassium nitrate, ammonium sulfate, and ammonium chloride produce cold. Further useful cooling agents are organic materials such as urea, and other inorganic salts such as ammonium bromide, ammonium iodide, potassium chloride, tin chloride dihydrate, diamminecobalt, dichlorocobalt hexahydrate, and nickel nitrate hexahydrate. Other suitable organic cooling agents include polyols such as xylitol, sorbitol, mannitol, and/or erythritol. A preferred agent is particulate ammonium nitrate, commercially available in the form of a low or high-density prill. The low-density prills may also include a clay binder, such as kaolin, at a low percentage by weight (from about 0.5 to about 5% by weight, often from about 1 to 3% by weight).

In a particular embodiment, the cooling composition is applied in solution form to the absorbent web, wherein the cooling agent recrystallizes on the web upon drying the solution. The solution may also employ a binder for enhancing the durability of the composition when applied to the cooling substrate. The binder may also serve as an adhesive for bonding one substrate to another substrate. Generally speaking, any of a variety of binders may be used in the cooling composition of the present invention. Suitable binders may include, for instance, those that become insoluble in water upon crosslinking. Crosslinking may be achieved in a variety of ways, including by reaction of the binder with a polyfunctional crosslinking agent. Examples of such crosslinking agents include, but are not limited to, dimethylol urea melamine-formaldehyde, urea-formaldehyde, polyamide epichlorohydrin, etc. In some embodiments, a polymer latex may be employed as the binder. Water-soluble organic polymers may also be employed as binders, either alone or in conjunction with the polymer latexes. For example, one class of suitable water-soluble organic polymers is polysaccharides and derivatives thereof.

The concentration of the binder in the cooling composition will generally vary based on the desired properties of the cooling substrate. For example, although relatively high binder concentrations may provide better physical properties for the cooling composition, they may likewise have an adverse effect on other properties, such as the absorptive capacity of the substrate to which it is applied. Conversely, relatively low binder concentrations may reduce the ability of the cooling agent component of the composition to remain affixed on the substrate. Thus, in most embodiments, the binder is present in the cooling composition solution in an amount from about 0.01 wt. % to about 20 wt. %, in some embodiments from about 0.1 wt. % to about 10 wt. %, and in some embodiments, from about 0.5 wt. % to about 5 wt. %.

Viscosity modifiers may be used in the cooling composition, for example, to adjust the viscosity of the coating formulation based on the desired coating process and/or performance of the coated cooling substrate. Suitable viscosity modifiers may include gums, such as xanthan gum. Binders, such as the cellulosic ethers, may also function as suitable viscosity modifiers. When employed, such additional components typically constitute less than about 5 wt. %, in some embodiments less than about 2 wt. %, and in some embodiments, from about 0.001 wt. % to about 1 wt. % of the coating.

The cooling composition also includes a hydrophobic agent that serves to decrease the wettability of the absorbent web. By so doing, the rate at which the aqueous liquid spreads throughout the absorbent web and contacts the cooling composition is decreased. Without the hydrophobic agent, the aqueous liquid spreads rapidly throughout the absorbent web and the reaction is relatively quick and pronounced, but not sustained. The presence of the hydrophobic agent provides a means by which the reaction rate can be controlled by varying the wetting characteristics of the medium (web) that carries the cooling composition. In this regard, desirable hydrophobic agents include polymer emulsions that are typically used as barrier coating materials. Such materials may include fluorochemicals, silicones, hydrocarbon olefin oligomers and polymers, styrene acrylics, vinyl acetate-ethylene copolymers, and the like. Particular commercially available compositions include EVOCAR emulsions from Dow Chemical, fluorochemical emulsions from Daikin, 3M and Dupont, wax emulsions from Michelman (including paraffin, polyethylene, polypropylene, carnauba, and amide). A polymer emulsion barrier coating, such as Airflex® EP1188 from Air Products and Chemicals, Inc. is another suitable hydrophobic agent.

Various types of porous substrates may serve as the absorbent web component of the cooling substrate combination.

For instance, nonwoven fabrics, woven fabrics, knit fabrics, paper web, film, absorbent foams, etc., may be applied with the cooling composition. When utilized, nonwoven fabrics may include, but are not limited to, spunbonded webs (apertured or non-apertured), meltblown webs, bonded carded webs, air-laid webs, coform webs, hydraulically entangled webs, and so forth. The absorbent web captures liquid to generate a uniform cooling effect in a device regardless of orientation or position of the web. The absorbent material may include an absorbent web formed using any technique, such as a dry-forming technique, an airlaying technique, a carding technique, a meltblown or spunbond technique, a wet-forming technique, a foam-forming technique, etc. The absorbent layer may contain cellulosic fibers, such as natural and/or synthetic fluff pulp fibers. The fluff pulp fibers may be kraft pulp, sulfite pulp, thermomechanical pulp, etc. In addition, the fluff pulp fibers may include high-average fiber length pulp, low-average fiber length pulp, or mixtures of the same. One example of suitable high-average length fluff pulp fibers includes softwood kraft pulp fibers.

In a particular embodiment, the substrate is a dual layer bonded carded web material of type used, for example, as surge layer materials in absorbent articles. Examples of these dual layer bonded carded webs may be found in U.S. Pat. No. 5,820,973 Heterogeneous Surge Material for Absorbent Articles, incorporated herein by reference for all purposes.

To apply the cooling composition to the absorbent web, the components may initially be dissolved or dispersed in a solvent. For example, one or more of the above-mentioned components may be mixed with a solvent, either sequentially or simultaneously, to form a coating formulation that may be easily applied to a substrate. Any solvent capable of dispersing or dissolving the components is suitable, for example water; alcohols such as ethanol or methanol; dimethylformamide; dimethyl sulfoxide; hydrocarbons such as pentane, butane, heptane, hexane, toluene and xylene; ethers such as diethyl ether and tetrahydrofuran; ketones and aldehydes such as acetone and methyl ethyl ketone; acids such as acetic acid and formic acid; and halogenated solvents such as dichloromethane and carbon tetrachloride; as well as mixtures thereof. In one particular embodiment, for example, water is used as the solvent so that an aqueous coating formulation is formed. Although the actual concentration of solvent (e.g., water) employed will generally depend on the type and amount of cooling agent and the substrate on which it is applied, it is nonetheless typically present in an amount from about 10 wt. % to about 80 wt. % of the coating formulation. The amount of the other components added to the coating formulation may vary depending on the amount of cooling desired, the wet pick-up of the application method utilized, etc.

The viscosity of the cooling composition formulation may be varied in accordance with the coating method to achieve the desired cooling profile as a function of the amount of the composition on the substrate. For instance, lower viscosities may be employed for saturation coating techniques (e.g., dip-coating), while higher viscosities may be employed for drop-coating techniques. If desired, thickeners or other viscosity modifiers may be employed in the coating formulation to increase or decrease viscosity. The coating formulation may have a solids content of from about 10% to about 80%, in some embodiments from about 30% to about 70%, and in some embodiments, from about 50% to about 60%. By varying the solids content of the coating formulation, the presence of the cooling agent and other components in the cooling composition may be controlled. For example, to form a cooling composition with a higher degree of cooling agent, the coating formulation may be provided with a relatively high solids content so that a greater percentage of the agent is incorporated into the composition during the application process. If desired, thickeners or other viscosity modifiers may be employed in the coating formulation to increase or decrease viscosity.

The cooling composition formulation may be applied to a substrate using any conventional technique, such as bar, roll, knife, curtain, print (e.g., rotogravure), spray, slot-die, drop-coating, or dip-coating techniques. The composition may be applied to one or both surfaces of the substrate. For example, the composition may be present only on the surface of the substrate that is adjacent the article to be cooled, or on both surfaces of the substrate. In addition, the composition may cover an entire surface of the substrate, or may only cover a portion of the surface.

Regardless of the manner in which the cooling composition is applied, the resulting cooling substrate is typically heated to a certain temperature to remove the solvent and re-crystallize the cooling agent in the form of a film-like coating over the fibers in the absorbent web. For example, the thermal substrate may be heated to a temperature of at least about 100° C., in some embodiments at least about 110° C., and in some embodiments, at least about 120° C. In this manner, the resulting dried cooling composition is anhydrous, i.e., generally free of water, and is distributed throughout the substrate in the form of a film-like network of re-crystallized cooling agent. By minimizing the amount of moisture, the composition is less likely to react prematurely and generate cold. Thus, the composition may remain inactive for extended periods until it is desired to use the cooling device.

The thickness of the cooling composition may also vary. For example, the thickness may range from about 0.01 millimeters to about 5 millimeters, in some embodiments, from about 0.01 millimeters to about 3 millimeters, and in some embodiments, from about 0.1 millimeters to about 2 millimeters. In some cases, a relatively thin coating may be employed (e.g., from about 0.01 millimeters to about 0.5 millimeters). Such a thin coating may enhance the flexibility of the substrate.

To maintain absorbency, porosity, flexibility, and/or some other characteristic of the substrate, it may sometimes be desired to apply the cooling composition so as to cover less than 100%, in some embodiments from about 10% to about 80%, and in some embodiments, from about 20% to about 60% of the area of one or more surfaces of the absorbent web. For instance, in one particular embodiment, the cooling composition is applied to the absorbent web in a defined pattern (e.g., reticular pattern, diamond-shaped grid, dots, and so forth). Such a patterned composition may provide sufficient cooling to the substrate without covering a substantial portion of the surface area of the substrate. This may be desired to optimize flexibility, absorbency, or other characteristics of the substrate. It should be understood, however, that the coating may also be applied uniformly to one or more surfaces of any number or combination of webs.

In addition, a patterned application of the cooling composition may also provide different cooling characteristics (functionality) to each zone. For example, in one embodiment, the substrate is treated with two or more patterns of coated regions that may or may not overlap. The regions may be on the same or different absorbent webs. One region may be coated with a first cooling composition, while another region is coated with a second different cooling composition. The first region may provide a rapid but relatively short cooling profile, while the second region generates a gradual but sustained cooling profile. In embodiments wherein different cooling compositions are applied to the same web, care might be necessary to separate the compositions during application and drying. In alternate embodiments, the different cooling compositions may be applied to different substrates.

The present invention is also directed to any manner of cooling device that incorporates one or more of the cooling substrate combinations described herein. Particular embodiments include a cooling sleeve or wrap to be applied against any desired body part or object, wherein the sleeve includes a shell member with the cooling substrate combination contained therein. Other materials may also be employed to improve or enhance application of cooling through the shell member to an article or body part. For example, any number or combination of thermal conductive and/or insulation material layers may be disposed within the interior space of the shell member. These materials may be employed to provide cooling to substantially only the inner face of the shell member that is placed against an article or body part. In an alternative arrangement, the shell member is reversible such that either face may provide the desired cooling effect, with the materials disposed within the shell member to provide cooling to both faces of the shell member.

In addition, substrates may be employed to aid in distributing liquid from the liquid source throughout the interior of the shell member to the cooling substrate to produce a more even cooling effect. Such materials may include, for example, a nonwoven web, a film, a channeled or embossed substrate, and any other material that serves to wick or channel liquid from one area to another without absorbing or retaining the liquid to any significant degree.

The shell member is not limited to any particular shape or material. In particular embodiments, the shell member is liquid impervious and comprises a thin, flexible, envelope-type structure. The shell member is formed of materials that are not deleteriously affected by any of the contents of the cooling composition, and which are resistant to the cold temperature produced by the device. The shell member may include a thermally conductive material at one or both interior surfaces. Such materials can be polymeric, and include ionomer film (for example, SURLYN available from DuPont), polyethylene, polypropylene, polyester (such as MYLAR film obtainable from DuPont) aluminum, aluminized polymer film, and other conventional plastic or other packaging materials suitable for containing cooled liquids, such as rubber, vinyl, or vinyl-coated fabric. In a preferred embodiment, the thermally conductive material is a metal foil, such as one composed substantially of aluminum or copper, or a metallized plastic film such as aluminized polyester.

An insulation material layer may be provided at the outer face of the shell member to insulate the user from the cold. This layer may also serve to present a soft, compliant, and functional surface to the user. This material may be, for example, a nonwoven material that is creped, embossed, textured, or otherwise presents a grip-enhanced surface to the user.

The shell member may be formed by a laminate material that includes a thermally conductive material laminated to an insulation layer material. For example, the shell member may be a laminate of a nonwoven insulation material and a thermally conductive film.

The shell member desirably has a thickness that permits the shell member to readily conform to the shape of the body part or object to be cooled. The shell member may be formed by separate material layers that are bonded together at the edges to form a hermetically sealed, substantially planar envelope. The edges of the material are bonded together by any suitable means, for example, soldering, heat sealing, ultrasonic welding, solvent welding, fold sealing, or the use of adhesives.

In still an alternate embodiment, the shell member may include a more rigid layer that defines a closed or open-ended configuration having dimensions to receive an article or body part (e.g., arm or foot) inserted therein. This layer may be, for example, an open or closed cell foam material. The interior space for receipt of the cooling substrate may be defined within this material, or may be defined between the inner surface (surface that faces the container) of the foam and a thermally conductive layer that is attached to the interior surface.

The activating liquid is supplied by the internal liquid source. In a particular embodiment, this source is defined by a compartment within the shell member that is opened or breached by manual manipulation of the shell member by the user. The barrier may be a wall formed of a material that allows its rupture, break, perforate, or otherwise be compromised by manual deformation of the shell member, for example upon the user compressing or twisting the shell member prior to placing the device against an object or body part. Any number and configuration of barrier walls may be formed in the interior of the shell member depending on the size of the thermal device and the volume of liquid to be delivered. In one embodiment, the barrier comprises a brittle or weakened wall extending between the interior surfaces of the shell member. In another embodiment, the barrier may be a frangible seal between the opposing interior faces of the shell member.

In other embodiments, the liquid source includes any combination of separate liquid filled "bladders" placed within the interior of the shell. These bladders may include, for example, liquid vials, pliable pouches, or any other suitable liquid container that is readily opened, broken, or otherwise breeched by external manual manipulation of the device.

It may be desired that the shell member have elastic properties, particularly in the embodiments wherein the shell member defines a closed cylindrical sleeve. In this regard, the shell member may be formed of any combination of conventional liquid impermeable elastomeric materials, such as an elastomeric film/nonwoven laminate.

Figure 1B:
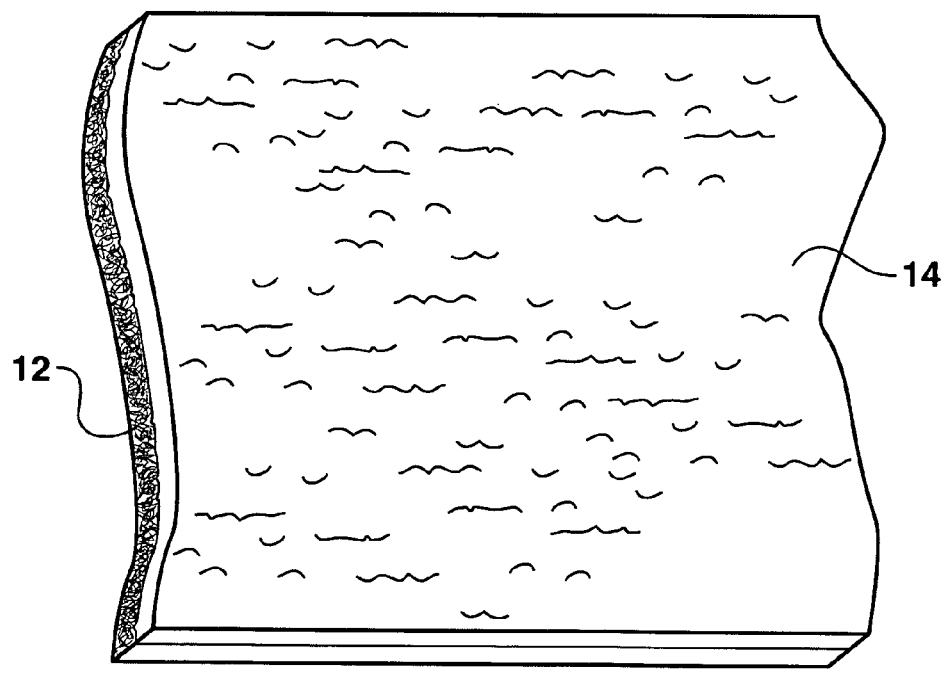
FIG. 1B is an enlarged perspective view of the coated portion of the substrate from FIG. 1A.

Various embodiments of a cooling substrate 10, and exemplary cooling device 100 incorporating the cooling substrate 10, in accordance with the invention are illustrated in the figures. FIGS. 1A, and 1B illustrate the substrate 10 as including a first absorbent web 12 of porous material, with a portion of the web 12 coated with a first cooling composition 14, as discussed above. FIG. 1B is an enlarged view of the coated portion of the web 12 that depicts the film-like network of cooling composition 14 in the web 12. This film-like network is generally continuous across the surface of the web 12, but is "rough" or contoured in that it also penetrates into the spaces between the fibers and "bridges" the fibers without penetrating completely through the web 12.

Figure 2A:
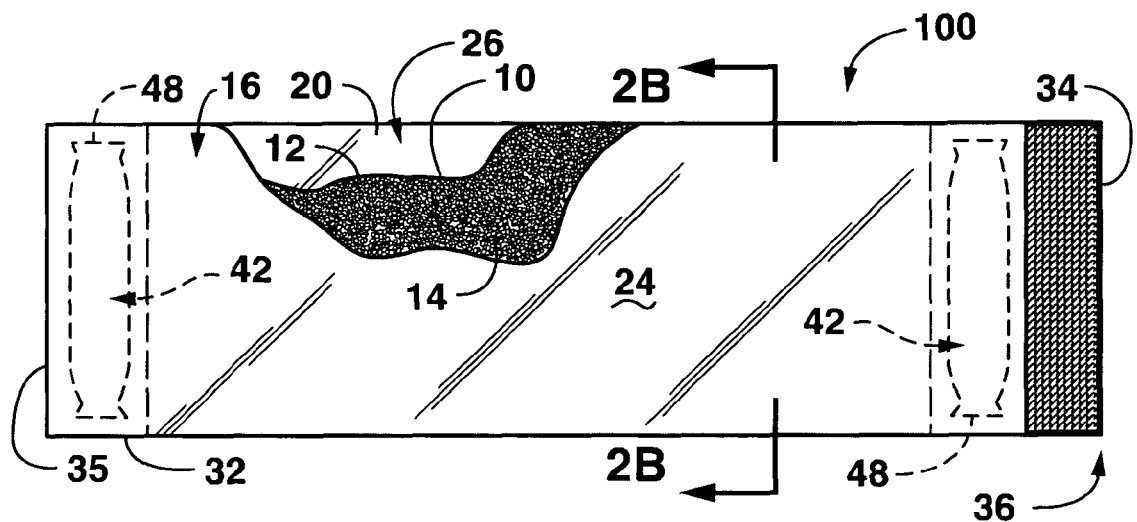
FIG. 2A is a perspective and partial cut-away view of a cooling device that incorporates a cooling substrate in accordance with the invention.
Figure 2B:
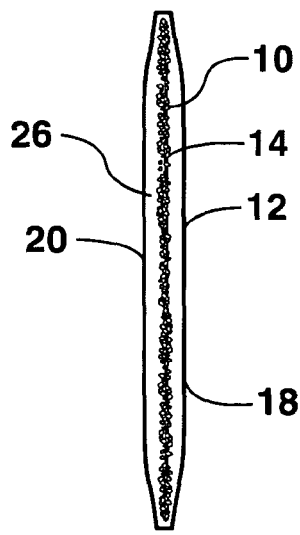
FIG. 2B is a cross-sectional view taken along the lines indicated in FIG. 2A.

FIGS. 2A and 2B illustrate a particular embodiment of a cooling device 100 in the form of a sleeve that may be applied around any object or body part to be cooled. The device 100 includes a shell member 16 formed from a first panel 18 and an opposite second panel 20 that define an interior space 26, with the cooling substrate 10 contained within this interior space. These panel members may be the same material, or different materials. The first panel 18 defines an inner face 24 that is disposed against the surface to be cooled when the device 100 is wrapped around or otherwise applied against the surface. The shell member 16 may define a generally flat, planar, flexible sleeve member 32 having opposite ends 34, 35. At one of the ends, or at both ends, any suitable attaching mechanism 36 is provided for securing the sleeve 32 around an object or body part. In the illustrated embodiment, the attaching mechanism 36 is a conventional hook-and-loop type of fastener wherein hooks are provided along the end 34 of the sleeve 32. These hooks engage directly against the outer surface material of the panel 20, or a separate landing zone of hook compatible material may be provided on the panel 20. In alternative embodiments, the attaching mechanism 36 may be a releasable adhesive, mechanical device, and so forth. It should be appreciated that the invention is not limited by any particular type of attaching mechanism for securing the flexible sleeve 32 around or to an object to be cooled.

Figure 3:
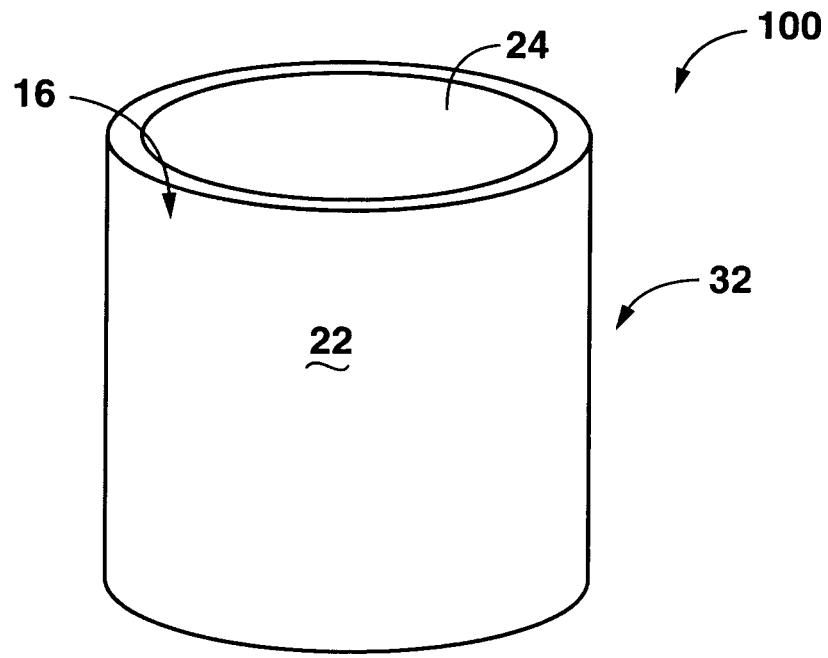
FIG. 3 is a perspective view of an alternative embodiment of a cooling device according to the invention in the form of a flexible closed-loop device.

FIG. 3 illustrates an alternative embodiment of a cooling device 100 wherein the shell member 16 is defined by a flexible sleeve member 32 that is formed into a closed-loop configuration. To use this device, the operator manipulates the sleeve member 32 into an open configuration, and subsequently slides an object or body part into the sleeve. This configuration may be particularly well suited as a therapeutic cooling device to treat sports injuries.

Figure 4:
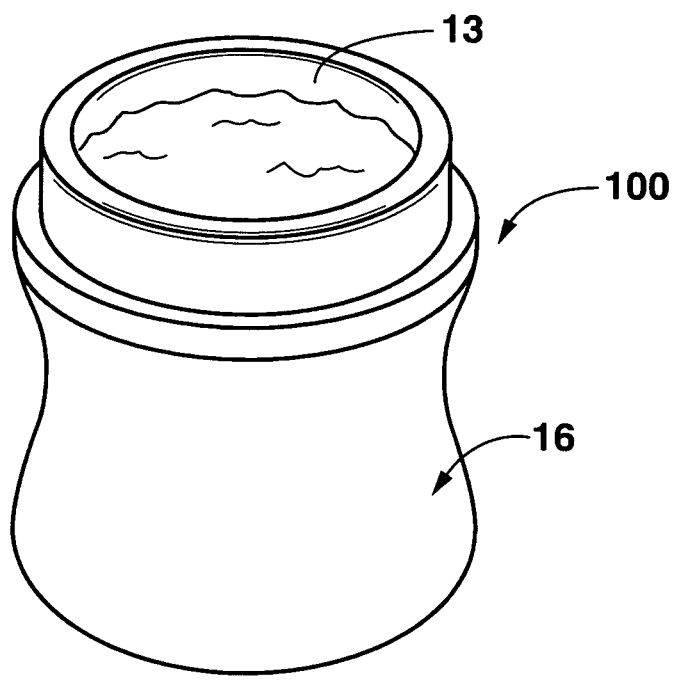
FIG. 4 is a perspective view of still another embodiment of a molded cooling device for a beverage container in accordance with the invention.

FIG. 4 illustrates an alternative embodiment of a cooling device 100 wherein the shell member 16 is defined by a molded body having sufficient rigidity so as to maintain a generally cylindrical open or closed-ended receptacle configuration. This embodiment may be used to place an object, such as a beverage cup or container 13, into the cooling device 100.

It should be appreciated that the cooling device 100 according to the invention is not limited to any particular shape, configuration, or appearance. The unique thermal aspects of the present invention may be incorporated into any conventional style of cooling pad, food product insulator, and so forth.

Referring again to FIG. 2A, the cooling substrate 10 desirably has a length and width dimension so as to completely encircle the object or body part once the sleeve member 32 is applied around the item. In this regard, the substrate 10 may have dimensions corresponding to the width and length dimensions of the interior space 26. It should be appreciated, however, that the invention encompasses alternative embodiments wherein the substrate is discontinuous or does not completely encircle the item.

An aqueous liquid source 42 is disposed within the interior space 26 of the shell member 16. In the embodiment illustrated in FIG. 2A, the liquid source 42 is provided by bladders 48 disposed generally adjacent the opposite ends of the flexible sleeve 32, or at any other location within the interior space 26. The bladders 48 are inserted between the panel members 18, 20, in construction of the cooling device 100. The bladders 48 are filled with an aqueous liquid, such as water, and rupture or burst upon sufficient pressure being applied thereto. To activate the device 100, a user simply grasps and squeezes the sleeve 32 at the ends thereof causing the bladders 48 to rupture and release the liquid contained therein. The liquid is then free to move within the interior space 26 and contact the cooling composition 14 applied to the cooling substrate 10. Desirably, the volume of liquid released from the bladders 48 is sufficient to saturate the absorbent web material of the cooling substrate 10 to ensure a complete and effective cooling reaction, while minimizing excess liquid that may tend to slosh around within the shell member 16.

In the embodiment of FIG. 2A, it is understood that the barrier member between the cooling substrate 10 and the liquid source 42 is the walls of the bladder 48 that rupture or otherwise break to release the liquid. Thus, in this embodiment, separate barrier walls or seals are not formed within the interior space 26 of the shell member 16.

Figure 5:
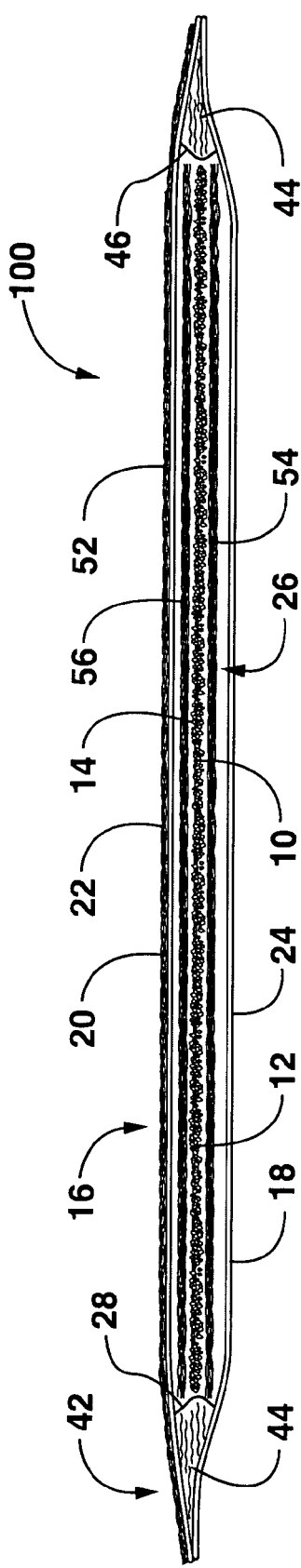
FIG. 5 is a cross-sectional view of a particular embodiment of a cooling device in accordance with the invention.

FIG. 5 illustrates an embodiment of a cooling device 100 wherein the opposite panels 18 and 20 define the shell member 16 and interior space 26. In this particular embodiment, the liquid source 42 is provided by compartments 44 formed at the longitudinal ends of the device by an integral barrier 46, such as barrier walls 28 that extend between the inner surfaces of the panels 18, 20. These walls 28 may be formed by any material that breaks or ruptures upon external pressure being applied to the sleeve at the ends thereof to activate the device 100. The walls 28 may be thinned or weakened as compared to the panel members 18, 20 to ensure that they rupture or break prior to compromising the integrity of the panel members.

As discussed in detail above, the shell member 16, particularly the panels 18 and 20, may be formed of various suitable materials. In the embodiment illustrated in FIG. 5, the panel 18 defining the inner face 24 of the cooling device 100 may be a liquid impermeable film. The opposite panel 20 may be a film/nonwoven laminate material wherein the nonwoven component of the laminate defines the outer face 22 that is presented to the user in use of the device. This nonwoven layer 22 presents a soft and compliant surface to the user, as compared to a film. The nonwoven layer may also serve as an insulation layer so that the user's hand is not exposed to the full cooling effect of the device 100.

Still referring to FIG. 5, various material layers may be included within the interior space 26 to provide desirable thermal characteristics. For example, material layer 54 may be a thermally conductive material. Material layer 56 may be a conductive material, or a material specifically designed to quickly conduct the fluid released from the compartments 44 along the longitudinal length of the device. This material layer 56 may be, for example, a hydrophilic material having channels or other liquid conveying structure embossed or otherwise formed therein.

Figure 6:
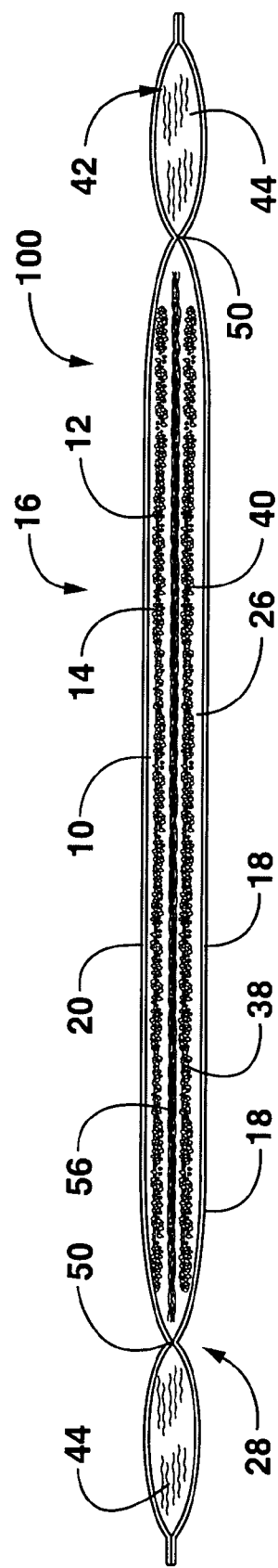
FIG. 6 is a cross-sectional view of an alternative embodiment of a cooling device in accordance with the invention.

FIG. 6 illustrates an embodiment of a cooling device 100 wherein the liquid source 42 is defined by compartments 44 formed at the longitudinal ends of the shell member 16. The compartments 44 are formed by frangible seals 50 defined between the opposite panels 18, 20. These seals 50 may be formed by welding, adhesive, bonding, and the like, and have a seal strength that is less than the seals between the panel members 18 and 20 at the ends thereof to ensure the integrity of the sleeve member 16. To activate the device 100, a user applies external pressure to the compartment 44 causing the frangible seals 50 to separate and release the liquid contained within the compartments 44.

In the embodiment of FIG. 6, the cooling substrate combination 10 includes a second absorbent web 38 provided with a second cooling composition 40. The web 38 and composition 40 may provide a different cooling profile as compared to the first web 12 and composition 14. As discussed above, different combinations of absorbent webs and cooling compositions may be provided to generate different cooling profiles. In the embodiment of FIG. 6, a material layer 56 is provided between the webs 12 and 38 and serves as a distribution layer to quickly channel the fluid from the compartments 44 along the longitudinal length of the substrates. The panel members 18 and 20 are formed, for example, of a thermally conductive and liquid impermeable film such that either surface may be applied against a body part or object. Thus, the embodiment of FIG. 6 is reversible and would include an appropriate attaching mechanism at one or both ends of the shell member 16.

Figure 7:
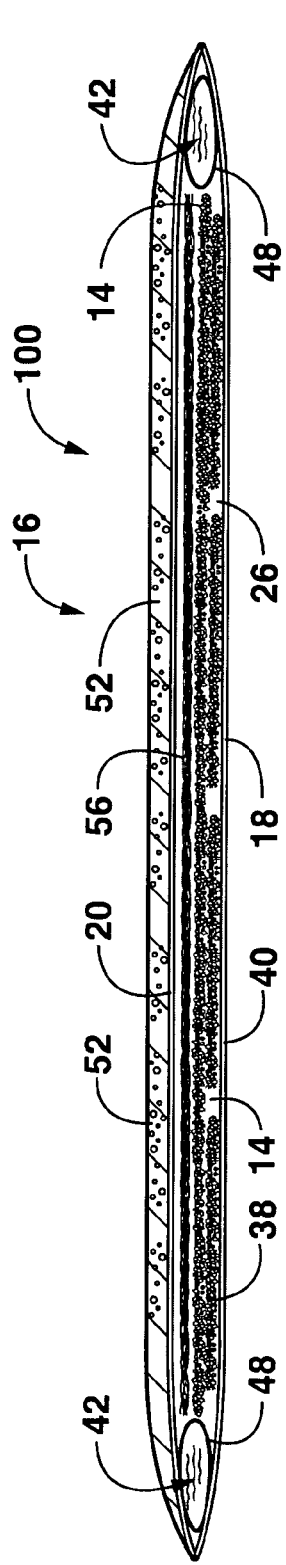
FIG. 7 is a cross-sectional view of still a different embodiment of a cooling device in accordance with the invention.

FIG. 7 illustrates an embodiment of a cooling device 100 wherein the panel 18 is defined by, for example, a liquid impermeable and thermally conductive film. The opposite panel 20 includes an interior film layer and an insulation layer 52 applied to the outer surface thereof. The insulation layer 52 may comprise, for example, a foam layer, and the entire panel member 20 may be a laminate of the film and foam material.

Still referring to the embodiment of FIG. 7, the liquid source 42 is defined by bladders 48 at the ends of the shell member 16. The cooling substrate combination includes a first absorbent web 14 and associated cooling composition, and a series of second absorbent webs 38 and associated cooling composition 40, which are also provided to produce a substantially different set of cooling characteristics as compared to the first web 14 and associated composition. For example, the cooling composition 40 may be void of a hydrophobic agent and may thus produce a more pronounced and rapid cooling effect as compared to the first web 14 and associated cooling composition. A distribution material layer 56 may also be included within the interior space 26 to readily channel and distribute the liquid released from the bladders 48 along the longitudinal length of the shell member 16.

Figure 8:
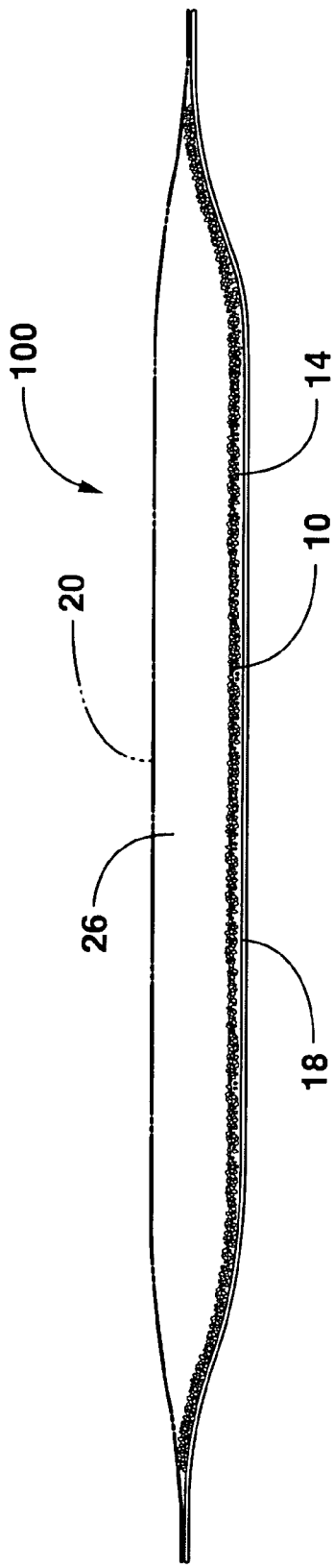
FIG. 8 is a partial cross-sectional view particularly illustrating an embodiment of a panel member that may be used as a shell member component in accordance with the invention.

FIG. 8 illustrates a particular embodiment of a panel member 18 that incorporates the cooling substrate 10 as an integral component thereof. In this particular embodiment, the panel member 18 may be a film/nonwoven laminate material, wherein the nonwoven component functions as the absorbent web and is coated with the cooling composition 14. Thus, in this particular embodiment, the cooling substrate 10 is not defined by a separate material layer disposed between opposite panel members.

The various layers and/or components of the cooling device may be assembled together using any known attachment means, such as adhesives, ultrasonic bonding, thermal bonds, etc. Suitable adhesives may include, for example, hot melted adhesives, pressure-sensitive adhesives, and so forth.

The present invention may be better understood with reference to the following examples.

Example 1

The ability to form a water activated cooling substrate was demonstrated. Initially, a bonded carded web fabric was cut into pieces that measured 7 inches in the cross machine direction and 12 inches in the machine direction. The bonded carded web fabric had a basis weight of 50 grams per square meter (50 gsm) and was made with a blend of 60% 1.5 denier FiberVisions ESC 215 bicomponent (PE sheath/PP core) fiber with 0.55% HR6 finish and 40% 6.0 denier Invista T-295 polyester fiber with 0.50% L1 finish.

An aqueous coating formulation was prepared as follows. In a 400 milliliter PYREX® beaker, 1.50 grams of xanthan gum (Verxan D from Cargill) was added to 298.5 grams of distilled water. The mixture was stirred for 1.5 hours and then left overnight. The following morning, the mixture was observed to be higher in viscosity. It was stirred for an additional 10 minutes and then the viscosity was measured at 1032 centipoise using a Brookfield DV-1 viscometer with an LV-4 spindle set at 100 rpm. Next, 120.7 grams of the xanthan gum/water solution were placed in a 250 milliliter PYREX® beaker, and while stirring, 80.2 grams of urea (Sigma, 99.5%) were slowly added. After the formulation had warmed to room temperature, the viscosity was measured at 248 centipoise using a Brookfield DV-1 viscometer with an LV-3 spindle set at 100 rpm. The calculated concentration of each component of the aqueous formulation is set forth below in Table 1.

TABLE 1

| Components of the Aqueous Formulation | |
|---|---|
| Component | Calculated Amount |
| Urea | 39.9% |
| Xanthan Gum | 0.3% |
| Water | 59.8% |

The aqueous formulation was applied to one side of the bonded carded web using a #60 single wound coating rod. The coated fabric pieces were placed in a laboratory oven at 110° C. for about 35 minutes to dry. The dried urea coating had the appearance of a film-like network which was interconnected throughout the fabric structure. The concentration of the components of the coating composition was calculated from the coated and dried fabric pieces (20.7±0.4 grams), the untreated pieces of fabric (2.8±0.1 grams), and the composition of the aqueous formulation. The results are set forth below in Table 2.

TABLE 2

| Components of the Coating Composition | |
|---|---|
| Component | Calculated Amount |
| Urea | 99.3% |
| Xanthan Gum | 0.7% |
| Solids Add-On Level | ~639% |

A sleeve structure (3"×11") was then designed for activating the cooling reaction. Specifically, the sleeve structure was produced with a material obtained from Ampac Flexibles. The material contained a film made with a 0.5 mil biaxial oriented nylon layer laminated adhesively to a 2.0 mil linear low density polyethylene layer which was laminated adhesively on the nylon side to a rib knit patterned spunbond nonwoven fabric (basis weight of 50 grams per square meter). The sleeve was constructed with the film layer on the inside and the fabric layer on the outside. The total basis weight of this film/fabric laminate was measured at 180 grams per square meter and the thickness was measured at 0.74 mm (0.029 in) using a Mitutoyo Digimatic Indicator. Six pieces (2" CD×7" MD) of the coated fabric (total weight of 20.9 grams) were placed inside of the sleeve. Three pieces were placed on each side of a bonded carded web fabric (60% 1.5 denier FiberVisions ESC 215 bicomponent (PE sheath/PP core) fiber with 0.55% HR6 finish, 40% 6.0 denier Invista T-295 polyester fiber with 0.50% L1 finish, total basis weight of 50 grams per square meter) with the coated side of each piece aligned to face the sleeve. Two water bags were also placed inside of the film sleeve. The water bags were made out of GF-14 film (a 1.25 mil low density polyethylene barrier film from Pliant Corp.) and each filled with 12.0 grams of water. The bags were constructed by folding over a 3.5-inch by 2.5-inch piece of the film and heat sealing two edges. The water was then added with a plastic syringe and the third edge was then heat sealed. The final dimensions of the bags were about 1.8 inches by 2.5 inches. A water bag was positioned at each end of the sleeve. The film/fabric laminate that formed the sleeve was also heat sealed to enclose the coated fabric pieces, the uncoated fabric piece, and the water bags.

Four type K thermocouples (OMEGA Engineering, Incorporated) were attached to the sleeve to monitor the temperature as a function of time. The sleeve was placed on a layer of bubble wrap. A fifth type K thermocouple was attached to the bubble wrap to monitor the background temperature. Data from the thermocouples was collected with a Pico® TC-08 eight channel thermocouple data logger which was attached to a computer. The cooling reaction was activated by squeezing the two water bags which broke at least one of the heat sealed edges of each bag and thus released the water. The data collection was started about 1 minute after breaking the water bags. FIG. 9A shows the cooling data. Note that a cooling effect was produced immediately after the fabrics inside of the sleeve were exposed to the water from the broken water bags. It can also be seen in FIG. 9A that the bottom of the sleeve, which is in contact with the bubble wrap and thus better insulated from air at ambient temperature, provides a lower temperature.

Example 2

The ability to form a water activated cooling substrate was demonstrated. Initially, a dual layer bonded carded web was cut into pieces that measured 7 inches in the cross machine direction and 8 inches in the machine direction. One side of the web contained 17 gsm of a 100% 1.5 denier FiberVisions ESC 215 bicomponent (PE sheath/PP core) fiber with 0.55% HR6 finish. The other side of the web contained 58 gsm of a blend of 40% 6.0 denier Invista T-295 polyester fiber with 0.50% L1 finish and 60% of a 28 denier FiberVisions ESC 236 bicomponent (PE sheath/PP core) fiber with 0.55% HR6 finish. Therefore, the total basis weight of the dual layer bonded carded web was 75 gsm.

An aqueous coating formulation was prepared as follows. In a 600 milliliter PYREX® beaker, 5.0 grams of xanthan gum (Verxan D from Cargill) was added to 295.0 grams of distilled water. The mixture was stirred for about 6 hours and then the viscosity was measured at about 4500 centipoise using a Brookfield DV-1 viscometer with an LV-4 spindle set at 100 rpm. Next, 250.0 grams of urea (Sigma, 99.5%) were slowly added and the formulation was stirred for about an hour and then left overnight. The following morning, the formulation was again stirred for about 25 minutes and then the viscosity was measured at about 2400 centipoise using a Brookfield DV-1 viscometer with an LV-4 spindle set at 100 rpm. The calculated concentration of each component of the aqueous formulation is set forth below in Table 3.

TABLE 3

Components of the Aqueous Formulation

| Component | Calculated Amount |
|---|---|
| Urea | 45.5% |
| Xanthan Gum | 0.9% |
| Water | 53.6% |

The aqueous formulation was applied to the polyester/bicomponent fiber side of the dual layer bonded carded web using a #60 single wound coating rod. The coated fabric pieces were placed in a laboratory oven at 110° C. for about 25 minutes to dry. The dried urea coating had the appearance of a film-like network which was interconnected throughout the fabric structure. The concentration of the components of the coating composition was calculated from the coated and dried fabric pieces (13.8±0.6 grams), the untreated pieces of fabric (2.3±0.1 grams), and the composition of the aqueous formulation. The results are set forth below in Table 4.

TABLE 4

Components of the Coating Composition

| Component | Calculated Amount |
|---|---|
| Urea | 98.0% |
| Xanthan Gum | 2.0% |
| Solids Add-On Level | ~501% |

The coated fabric of Example 2 was evaluated for wettability to water. Seven water drops were placed across the 7-inch cross directional width of a coated fabric piece using a disposable plastic pipette. The coated fabric piece was immediately wetted out by each of the seven drops of water. Therefore, the urea in the coated fabric of Example 2 is immediately exposed to water and is expected to provide immediate cooling.

Example 3

The ability to form a water activated cooling substrate was demonstrated. Initially, a dual layer bonded carded web was cut into pieces that measured 7 inches in the cross machine direction and 8 inches in the machine direction. One side of the web contained 17 gsm of a 100% 3.0 denier FiberVisions ESC 233 bicomponent (PE sheath/PP core) fiber with 0.55% HR6 finish. The other side of the web contained 100 gsm of a blend of 50% 15 denier Invista T-295 polyester fiber with 0.50% L1 finish and 50% of a 6.0 denier FiberVisions ESC 236 bicomponent (PE sheath/PP core) fiber with 0.55% HR6 finish. Therefore, the total basis weight of the dual layer bonded carded web was 117 gsm.

An aqueous coating formulation was prepared as follows. In a 400 milliliter PYREX® beaker, 366.9 grams of the urea+xanthan gum/distilled water formulation described in Table 3 of Example 2 was mixed with 29.3 grams of Michem® Lube 723 (a nonionic paraffin wax emulsion with 30% solids, available from Michelman, Inc.). The mixture was stirred for about 30 minutes and then the viscosity was measured at about 1750 centipoise using a Brookfield DV-1 viscometer with an LV-4 spindle set at 100 rpm. The calculated concentration of each component of the aqueous formulation is set forth below in Table 5.

TABLE 5

Components of the Aqueous Formulation

| Component | Calculated Amount |
|---|---|
| Urea | 42.1% |
| Michem ® Lube 723 | 2.2% |
| Xanthan Gum | 0.8% |
| Water | 54.9% |

The aqueous formulation was applied to the polyester/bicomponent fiber side of the dual layer bonded carded web using a #60 single wound coating rod. The coated fabric pieces were placed in a laboratory oven at 110° C. for about 75 minutes to dry. The dried urea coating had the appearance of a film-like network which was interconnected throughout the fabric structure. The concentration of the components of the coating composition was calculated from the coated and dried fabric pieces (28.6±0.6 grams), the untreated pieces of fabric (4.05±0.04 grams), and the composition of the aqueous formulation. The results are set forth below in Table 6.

TABLE 6

Components of the Coating Composition

| Component | Calculated Amount |
|---|---|
| Urea | 93.3% |
| Michem ® Lube 723 | 4.8% |
| Xanthan Gum | 1.9% |
| Solids Add-On Level | ~605% |

The coated fabric of Example 3 was evaluated for wettability to water. Seven water drops were placed across the 7-inch cross directional width of a coated fabric piece using a disposable plastic pipette. The coated fabric piece initially held out each of the seven drops of water. For example, the drops of water were initially beaded on the surface of the coated fabric piece and then began to partially spread on the surface after about 5 seconds. After 1 minute, the drops of water were still only partially spread on the surface of the coated fabric piece. Therefore, the urea in the coated fabric of Example 3 is not immediately exposed to water and is expected to provide a delayed cooling response.

Example 4

A sleeve structure (3"×10.8") was designed for activating the cooling reaction for the coated fabrics of Examples 2 and 3. This sleeve structure was produced with a material obtained from Ampac Flexibles, which is described in Example 1. Two pieces (2.2" CD×7" MD) of the coated fabric of Example 2 (total weight of 9.0 grams) and two pieces (2.2" CD×7" MD) of the coated fabric of Example 3 (total weight of 17.5 grams) were placed inside of the sleeve. The Example 3 pieces were first placed together with the coated side of each facing outward towards the sleeve. Then, each of the two Example 2 pieces was placed on an Example 3 piece with the coated side of Example 2 facing outward towards the sleeve. Two water bags were also placed inside of the film sleeve. The water bags were made out of GF-14 film (a 1.25 mil low density polyethylene barrier film from Pliant Corp.). One bag was filled with 15.2 grams of water and other bag was filled with 16.4 grams. The bags were constructed by folding over a 3.5-inch by 2.2-inch piece of the film and heat sealing two edges. The water was then added with a plastic syringe and the third edge was then heat sealed. The final dimensions of the bags were about 1.5 inches by 2.2 inches. A water bag was positioned at each end of the sleeve. The film/fabric laminate that formed the sleeve was also heat sealed to enclose the coated fabric pieces and the water bags. The final seal was made after evacuating the air from the sleeve using a Fuji Impulse V-300 Vacuum Sealer.

Four type K thermocouples (OMEGA Engineering, Incorporated) were attached to the sleeve to monitor the temperature as a function of time, as described in Example 1. The sleeve was placed on a layer of bubble wrap. A fifth type K thermocouple was attached to the bubble wrap to monitor the background temperature. The cooling reaction was activated by squeezing the two water bags which broke at least one of the heat sealed edges of each bag and thus released the water. The data collection was started about 1 minute before breaking the water bags. FIG. 9B shows the cooling data. Note that a cooling effect was produced within several minutes of exposing the fabrics inside of the sleeve to the water from the broken water bags. It can also be seen in FIG. 9B that the cooling response curve for the Example 4 sleeve maintains a reduced temperature for a longer period of time relative to the Example 1 sleeve (FIG. 9A). The improved (level) cooling profile demonstrated by the Example 4 sleeve can be attributed to the slower wetting Example 3 coated fabric pieces. Therefore, modifying the Example 3 urea coating by adding the Michem® Lube 723 paraffin wax to retard wetting by water provides a way to extend the cooling response.

Example 5

The ability to form a water activated cooling substrate was demonstrated. Initially, a dual layer bonded carded web was cut into pieces that measured 7 inches in the cross machine direction and 8 inches in the machine direction. One side of the web contained 17 gsm of a 100% 1.5 denier FiberVisions ESC 215 bicomponent (PE sheath/PP core) fiber with 0.55% HR6 finish. The other side of the web contained 58 gsm of a blend of 40% 6.0 denier Invista T-295 polyester fiber with 0.50% L1 finish and 60% of a 28 denier FiberVisions ESC 236 bicomponent (PE sheath/PP core) fiber with 0.55% HR6 finish. Therefore, the total basis weight of the dual layer bonded carded web was 75 gsm.

An aqueous coating formulation was prepared as follows. In a 600 milliliter PYREX® beaker, 5.0 grams of xanthan gum (Verxan D from Cargill) was added to 295.0 grams of distilled water. The mixture was stirred for about 2 hours and then the viscosity was measured at about 6000 centipoise using a Brookfield DV-1 viscometer with an LV-4 spindle set at 100 rpm. Next, 250.2 grams of ammonium nitrate (Sigma-Aldrich, 98+%) were slowly added and the formulation was stirred for about 3 hours. The viscosity was then measured at about 2175 centipoise using a Brookfield DV-1 viscometer with an LV-4 spindle set at 100 rpm. The calculated concentration of each component of the aqueous formulation is set forth below in Table 7.

TABLE 7

Components of the Aqueous Formulation

| Component | Calculated Amount |
|---|---|
| Ammonium Nitrate | 45.5% |
| Xanthan Gum | 0.9% |
| Water | 53.6% |

The aqueous formulation was applied to the polyester/bicomponent fiber side of the dual layer bonded carded web using a #60 single wound coating rod. The coated fabric pieces were placed in a laboratory oven at 110° C. for about 20 minutes to dry. The dried ammonium nitrate coating had the appearance of a film-like network which was interconnected throughout the fabric structure. The concentration of the components of the coating composition was calculated from the coated and dried fabric pieces (13.4±0.6 grams), the untreated pieces of fabric (2.2±0.1 grams), and the composition of the aqueous formulation. The results are set forth below in Table 8.

TABLE 8

Components of the Coating Composition

| Component | Calculated Amount |
|---|---|
| Ammonium Nitrate | 98.0% |
| Xanthan Gum | 2.0% |
| Solids Add-On Level | ~510% |

The coated fabric of Example 5 was evaluated for wettability to water. Seven water drops were placed across the 7-inch cross directional width of a coated fabric piece using a disposable plastic pipette. The coated fabric piece was immediately wetted out by each of the seven drops of water. Therefore, the ammonium nitrate in the coated fabric of Example 5 is immediately exposed to water and is expected to provide immediate cooling.

Example 6

The ability to form a water activated cooling substrate was demonstrated. Initially, a dual layer bonded carded web was cut into pieces that measured 7.5 inches in the cross machine direction and 8 inches in the machine direction. One side of the web contained 17 gsm of a 100% 3.0 denier FiberVisions ESC 233 bicomponent (PE sheath/PP core) fiber with 0.55% HR6 finish. The other side of the web contained 100 gsm of a blend of 50% 15 denier Invista T-295 polyester fiber with 0.50% L1 finish and 50% of a 6.0 denier FiberVisions ESC 236 bicomponent (PE sheath/PP core) fiber with 0.55% HR6 finish. Therefore, the total basis weight of the dual layer bonded carded web was 117 gsm.

An aqueous coating formulation was prepared as follows. In a 400 milliliter PYREX® beaker, 373.5 grams of the ammonium nitrate+xanthan gum/distilled water formulation described in Table 7 of Example 5 was mixed with 30.1 grams of Michem® Lube 723 (a nonionic paraffin wax emulsion with 30% solids, available from Michelman, Inc.). The mixture was stirred for about 1.5 hours and then the viscosity was measured at about 2750 centipoise using a Brookfield DV-1 viscometer with an LV-4 spindle set at 100 rpm. The calculated concentration of each component of the aqueous formulation is set forth below in Table 9.

TABLE 9

Components of the Aqueous Formulation

| Component | Calculated Amount |
| --- | --- |
| Ammonium Nitrate | 42.1% |
| Michem ® Lube 723 | 2.2% |
| Xanthan Gum | 0.8% |
| Water | 54.9% |

The aqueous formulation was applied to the polyester/bicomponent fiber side of the dual layer bonded carded web using a #60 single wound coating rod. The coated fabric pieces were placed in a laboratory oven at 110° C. for about 75 minutes to dry. The dried ammonium nitrate coating had the appearance of a film-like network which was interconnected throughout the fabric structure. The concentration of the components of the coating composition was calculated from the coated and dried fabric pieces (28.3±0.7 grams), the untreated pieces of fabric (4.2±0.1 grams), and the composition of the aqueous formulation. The results are set forth below in Table 10.

TABLE 10

Components of the Coating Composition

| Component | Calculated Amount |
| --- | --- |
| Ammonium Nitrate | 93.2% |
| Michem ® Lube 723 | 4.9% |
| Xanthan Gum | 1.9% |
| Solids Add-On Level | ~565% |

The coated fabric of Example 6 was evaluated for wettability to water. Eight water drops were placed across the 7.5-inch cross directional width of a coated fabric piece using a disposable plastic pipette. The coated fabric piece initially held out each of the eight drops of water. For example, the drops of water were initially beaded on the surface of the coated fabric piece and then were moderately spread on the surface after about 15 seconds. Therefore, the ammonium nitrate in the coated fabric of Example 6 is not immediately exposed to water and is expected to provide a delayed cooling response.

Example 7

The ability to form a water activated cooling substrate was demonstrated. Initially, a dual layer bonded carded web was cut into a piece that measured 5.5 inches in the cross machine direction and 13.5 inches in the machine direction. One side of the web contained 17 gsm of a 100% 3.0 denier FiberVisions ESC 233 bicomponent (PE sheath/PP core) fiber with 0.55% HR6 finish. The other side of the web contained 100 gsm of a blend of 50% 15 denier Invista T-295 polyester fiber with 0.50% L1 finish and 50% of a 6.0 denier FiberVisions ESC 236 bicomponent (PE sheath/PP core) fiber with 0.55% HR6 finish. Therefore, the total basis weight of the dual layer bonded carded web was 117 gsm.

An aqueous coating formulation was prepared as follows. In a 600 milliliter PYREX® beaker, 5.0 grams of xanthan gum (Verxan D from Cargill) was added to 295.3 grams of distilled water. The mixture was stirred for about 2.5 hours and then left overnight until further use. The following morning, the mixture was stirred for several minutes and then the viscosity was measured at about 5550 centipoise using a Brookfield DV-1 viscometer with an LV-4 spindle set at 100 rpm. Next, 149.7 grams of the xanthan gum/water solution were placed in a 400 milliliter PYREX® beaker, and while stirring, 125.2 grams of ammonium nitrate (Sigma-Aldrich, 98+%) were slowly added. After stirring the ammonium nitrate+xanthan gum/water solution for about 90 minutes, the viscosity was then measured at about 2250 centipoise using a Brookfield DV-1 viscometer with an LV-4 spindle set at 100 rpm. Next, in a 250 milliliter PYREX® beaker, 33.5 grams of Michem® Lube 723 (a nonionic paraffin wax emulsion with 30% solids, available from Michelman, Inc.) was added to 188.6 grams of the ammonium nitrate+xanthan gum/water solution. After about 40 minutes of stirring, the viscosity of the final formulation was measured at about 2100 centipoise using a Brookfield DV-1 viscometer with an LV-4 spindle set at 100 rpm. The calculated concentration of each component of the aqueous formulation is set forth below in Table 11.

TABLE 11

Components of the Aqueous Formulation

| Component | Calculated Amount |
| --- | --- |
| Ammonium Nitrate | 38.6% |
| Michem ® Lube 723 | 4.5% |
| Xanthan Gum | 0.8% |
| Water | 56.1% |

The aqueous formulation was applied to the polyester/bicomponent fiber side of the dual layer bonded carded web using a #60 single wound coating rod. The coated fabric piece was placed in a laboratory oven at 110° C. for about 45 minutes to dry. The dried ammonium nitrate coating had the appearance of a film-like network which was interconnected throughout the fabric structure. The concentration of the components of the coating composition was calculated from the coated and dried fabric piece (27.4 grams), the untreated piece of fabric (5.3 grams), and the composition of the aqueous formulation. The results are set forth below in Table 12.

TABLE 12

Components of the Coating Composition

| Component | Calculated Amount |
|---|---|
| Ammonium Nitrate | 88.1% |
| Michem ® Lube 723 | 10.2% |
| Xanthan Gum | 1.7% |
| Solids Add-On Level | ~417% |

The coated fabric of Example 7 was evaluated for wettability to water. Six water drops were placed across the 5.5-inch cross directional width of the coated fabric piece using a disposable plastic pipette. The drops of water were observed to bead or only partially spread after contacting the surface of the coated fabric piece for 1 minute. Therefore, the ammonium nitrate in the coated fabric of Example 7 is not immediately exposed to water and is expected to provide a delayed cooling response.

Example 8

A sleeve structure (2.8"×11") was designed for activating the cooling reaction for the coated fabrics of Examples 5, 6, and 7. This sleeve structure was produced with a material obtained from Ampac Flexibles, which is described in Example 1. Two pieces (2.2" CD×7" MD) of the coated fabric of Example 5 (total weight of 8.0 grams), one piece (2.2" CD×7" MD) of the coated fabric of Example 6 (8.3 grams), and one piece (2.2" CD×7" MD) of the coated fabric of Example 7 (6.4 grams) were placed inside of the sleeve. The Example 6 and 7 pieces were first placed together with the coated side of each facing outward towards the sleeve. Then, an Example 5 piece was placed on the Example 6 and 7 pieces with the coated side of Example 5 facing outward towards the sleeve. Two water bags were also placed inside of the film sleeve. The water bags were made out of GF-14 film (a 1.25 mil low density polyethylene barrier film from Pliant Corp.). One bag was filled with 16.8 grams of water and other bag was filled with 17.3 grams. The bags were constructed by folding over a 3.5-inch by 2.2-inch piece of the film and heat sealing two edges. The water was then added with a plastic syringe and the third edge was then heat sealed. The final dimensions of the bags were about 1.9 inches by 2.2 inches. A water bag was positioned at each end of the sleeve. The film/fabric laminate that formed the sleeve was also heat sealed to enclose the coated fabric pieces and the water bags. The final seal was made after evacuating the air from the sleeve using a Fuji Impulse V-300 Vacuum Sealer.

Four type K thermocouples (OMEGA Engineering, Incorporated) were attached to the sleeve to monitor the temperature as a function of time, as described in Example 1. The sleeve was placed on a layer of bubble wrap. A fifth type K thermocouple was attached to the bubble wrap to monitor the background temperature. The cooling reaction was activated by squeezing the two water bags which broke at least one of the heat sealed edges of each bag and thus released the water. The data collection was started about 1 minute before breaking the water bags. FIG. 9C shows the cooling data. Note that a cooling effect was produced within several minutes of exposing the fabrics inside of the sleeve to the water from the broken water bags. It can also be seen in FIG. 9C that the cooling response curve for the Example 8 sleeve maintains a constant low temperature for at least about 15 minutes. The improved (level) cooling profile demonstrated by the Example 8 sleeve can be attributed to the slower wetting Examples 6 and 7 coated fabric pieces. Therefore, modifying the Examples 6 and 7 ammonium nitrate coating by adding the Michem® Lube 723 paraffin wax to retard wetting by water provides a way to extend the cooling response.

Example 9

The ability to form a water activated cooling substrate was demonstrated. Initially, a dual layer bonded carded web was cut into a piece that measured 7 inches in the cross machine direction and 9 inches in the machine direction. One side of the web contained 17 gsm of a 100% 3.0 denier FiberVisions ESC 233 bicomponent (PE sheath/PP core) fiber with 0.55% HR6 finish. The other side of the web contained 50 gsm of a blend of 50% 15 denier Invista T-295 polyester fiber with 0.50% L1 finish and 50% of a 15 denier FiberVisions ESC 236 bicomponent (PE sheath/PP core) fiber with 0.55% HR6 finish. Therefore, the total basis weight of the dual layer bonded carded web was 67 gsm.

An aqueous coating formulation was prepared as follows. In a 600 milliliter PYREX® beaker, 7.6 grams of xanthan gum (Verxan D from Cargill) was added to 442.5 grams of distilled water. The mixture was stirred for about 2.5 hours and then the viscosity was measured at about 5500 centipoise using a Brookfield DV-1 viscometer with an LV-4 spindle set at 100 rpm. Next, 375.0 grams of urea (micro prilled from Yara Canada) were slowly added and the formulation was stirred for about an hour and then left overnight. The following morning, the viscosity of the formulation was measured at about 1580 centipoise using a Brookfield DV-1 viscometer with an LVA spindle set at 100 rpm. Next, while stirring, 32.8 grams of Airflex® EP1188 (a vinyl acetate-ethylene copolymer emulsion from Air Products and Chemicals, Inc.) were added to 286.4 grams of the urea+xanthan gum/water formulation. Finally, while stirring, 24.1 grams of glycerol (Sigma-Aldrich, 99.5+%, A.C.S. reagent) were added to 197.8 grams of the urea+EP1188+xanthan gum/water formulation. The viscosity of this final formulation was measured at about 1285 centipoise using a Brookfield DV-1 viscometer with an LV-4 spindle set at 100 rpm. The calculated concentration of each component of the aqueous formulation is set forth below in Table 13.

TABLE 13

Components of the Aqueous Formulation

| Component | Calculated Amount |
|---|---|
| Urea | 36.3% |
| Xanthan Gum | 0.7% |
| Airflex ® EP1188 | 4.2% |
| Glycerol | 10.9% |
| Water | 47.9% |

The aqueous formulation was applied to the polyester/bicomponent fiber side of the dual layer bonded carded web using a #60 single wound coating rod. The coated fabric piece was placed in a laboratory oven at 110° C. for about 75 minutes to dry. The dried urea coating had the appearance of a film-like network which was interconnected throughout the fabric structure. The addition of glycerol also improved the flexibility of the coated fabric. The concentration of the components of the coating composition was calculated from the coated and dried fabric piece (27.5 grams), the untreated piece of fabric (2.4 grams), and the composition of the aqueous formulation. The results are set forth below in Table 14.

TABLE 14

Components of the Coating Composition

| Component | Calculated Amount |
|---|---|
| Urea | 69.7% |
| Xanthan Gum | 1.4% |
| Airflex ® EP1188 | 8.0% |
| Glycerol | 20.9% |
| Solids Add-On Level | ~1038% |

Example 10

The ability to form a water activated cooling substrate was demonstrated. Initially, a dual layer bonded carded web was cut into a piece that measured 7 inches in the cross machine direction and 9 inches in the machine direction. One side of the web contained 17 gsm of a 100% 3.0 denier FiberVisions ESC 233 bicomponent (PE sheath/PP core) fiber with 0.55% HR6 finish. The other side of the web contained 100 gsm of a blend of 50% 15 denier Invista T-295 polyester fiber with 0.50% L1 finish and 50% of a 6.0 denier FiberVisions ESC 236 bicomponent (PE sheath/PP core) fiber with 0.55% HR6 finish. Therefore, the total basis weight of the dual layer bonded carded web was 117 gsm.

The aqueous formulation described in Example 9 and listed in Table 13 was applied to the polyester/bicomponent fiber side of the dual layer bonded carded web using a #60 single wound coating rod. The coated fabric piece was placed in a laboratory oven at 110° C. for about 1.5 hours to dry. The dried urea coating had the appearance of a film-like network which was interconnected throughout the fabric structure. The addition of glycerol also improved the flexibility of the coated fabric. The concentration of the components of the coating composition was calculated from the coated and dried fabric piece (37.0 grams), the untreated piece of fabric (4.5 grams), and the composition of the aqueous formulation. The results are set forth below in Table 15.

TABLE 15

Components of the Coating Composition

| Component | Calculated Amount |
|---|---|
| Urea | 69.7% |
| Xanthan Gum | 1.4% |
| Airflex ® EP1188 | 8.0% |
| Glycerol | 20.9% |
| Solids Add-On Level | ~718% |

The coated fabric of Example 10 was evaluated for wettability to water. Drops of water were placed across the 7-inch cross directional width of the coated fabric piece using a disposable plastic pipette. The water did not immediately absorb into the coated fabric piece, which suggests the urea in the coating will not be immediately exposed to water. Therefore, the coated fabric of Example 10 is expected to provide a delayed cooling response.

Example 11

A sleeve structure (2.8"×11") was designed for activating the cooling reaction for the coated fabrics of Examples 9 and 10. This sleeve structure was produced with a material obtained from Ampac Flexibles, which is described in Example 1. Two pieces (2.2" CD×7" MD) of the coated fabric of Example 9 (total weight of 15.1 grams) and two pieces (2.2" CD×7" MD) of the coated fabric of Example 10 (total weight of 19.8 grams) were placed inside of the sleeve. The Example 9 pieces were first placed together with the coated side of each facing the same direction. Then, each of the Example 10 pieces was placed on an Example 9 piece. The coated side of the Example 10 pieces also faced the same direction as the coated side for the Example 9 pieces. Two water bags were also placed inside of the film sleeve. The water bags were made out of GF-14 film (a 1.25 mil low density polyethylene barrier film from Pliant Corp.). One bag was filled with 17.0 grams of water and other bag was filled with 18.4 grams. The bags were constructed by folding over a 3.5-inch by 2.2-inch piece of the film and heat sealing two edges. The water was then added with a plastic syringe and the third edge was then heat sealed. The final dimensions of the bags were about 1.9 inches by 2.2 inches. A water bag was positioned at each end of the sleeve. The film/fabric laminate that formed the sleeve was also heat sealed to enclose the coated fabric pieces and the water bags. The final seal was made after evacuating the air from the sleeve using a Fuji Impulse V-300 Vacuum Sealer.

Four type K thermocouples (OMEGA Engineering, Incorporated) were attached to the sleeve to monitor the temperature as a function of time, as described in Example 1. The sleeve was placed on a layer of bubble wrap. A fifth type K thermocouple was attached to the bubble wrap to monitor the background temperature. The cooling reaction was activated by squeezing the two water bags resulting in at least one of the heat sealed edges of each bag rupturing and releasing the water. The data collection was started about 1 minute before breaking the water bags. FIG. 9D shows the cooling data. Note that a cooling effect was produced within several minutes of exposing the fabrics inside of the sleeve to the water from the broken water bags. It can also be seen in FIG. 9D that the cooling response curve for the Example 11 sleeve maintains a constant low temperature for at least about 15 minutes. The improved (level) cooling profile demonstrated by the Example 11 sleeve can be attributed to the slower wetting Examples 9 and 10 coated fabric pieces. Therefore, modifying the Examples 9 and 10 urea coating by adding the Airflex® EP1188 (a vinyl acetate-ethylene copolymer) to retard wetting by water provides a way to extend the cooling response.

What is claimed is:

1. A cooling device, comprising:
    a shell member having an outer face and an inner face disposed against a surface to be cooled in use of said device, said shell member defining an interior space;
    a cooling substrate combination disposed within said interior space, said cooling substrate comprising a first absorbent web of porous material having a first cooling composition applied thereto in a dried substantially film-like network distributed throughout said web, said cooling composition comprising a cooling agent that is activated by contact with an aqueous liquid and a hydrophobic agent present in an effective amount to inhibit wetting of said web and prolong a cooling reaction generated when said substrate is contacted with the aqueous liquid;
    an aqueous liquid source disposed within said interior space and separated from said first cooling substrate by a barrier member; and said device activated by manual manipulation to breach said barrier member causing liquid from said liquid source to move within said interior space to contact and activate said first cooling composition whereby a cooling reaction is generated.

2. The cooling device of claim 1, wherein said first cooling composition is applied to said absorbent web as an aqueous solution that dries to form said film-like network.

3. The cooling device of claim 1, wherein said cooling agent comprises one of an inorganic salt or an organic material, and said hydrophobic agent comprises a polymer emulsion that decreases the wettability of said absorbent web.

4. The cooling device of claim 3, wherein said cooling agent comprises at least about 50% by weight of said cooling composition, and said hydrophobic agent comprises between about 0.5% to about 10.0% by weight of said first cooling composition.

5. The cooling device of claim 1, wherein said first cooling composition produces a first cooling profile, and wherein said cooling substrate combination further comprises a second cooling composition that produces a second cooling profile that is more rapid as compared to said first cooling profile, said second cooling composition comprising a cooling agent that is activated by contact with an aqueous liquid upon activation of said device.

6. The cooling device of claim 5, wherein said second cooling composition further comprises a lesser amount of hydrophobic agent than said first cooling composition.

7. The cooling device of claim 5, wherein said cooling substrate combination further comprises a second absorbent web of porous material within said interior space, said second cooling composition applied to said second absorbent web in a substantially film-like network distributed throughout said porous material.

8. The cooling device as in claim 1, wherein said shell member comprises a flexible and conformable sleeve member that conforms around an object to be cooled, said first cooling substrate comprising a flexible material so as to conform with said shell member around the object.

9. The cooling device as in claim 1, wherein said liquid source comprises at least one bladder inserted into said interior space, said bladder separating or breakable upon manual manipulation of said device.

10. The cooling device as in claim 1, further comprising any combination of insulation material layers and thermal conductive material layers within said interior space so as to direct the generated cooling effect to said inner face.

11. The cooling device as in claim 1, wherein substantially all of said liquid from said liquid source is absorbed by said cooling substrate combination so that excess liquid is not held within said interior space after activation of said device.

12. The cooling device as in claim 1, wherein said cooling substrate combination comprises a separate material disposed within said interior space between interior faces of said shell member.

* * * * *